(12) United States Patent
Kennis et al.

(10) Patent No.: US 6,495,555 B1
(45) Date of Patent: Dec. 17, 2002

(54) TRICYCLIC Δ-3-PIPERIDINES AS $\alpha_2$-ANTAGONISTS

(75) Inventors: Ludo Edmond Josephine Kennis, Turnhout (BE); Frans Maria Alfons Van den Keybus, Essen (BE); Josephus Carolus Mertens, Oud-Turnhout (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 09/806,547

(22) PCT Filed: Oct. 1, 1999

(86) PCT No.: PCT/EP99/07419
§ 371 (c)(1),
(2), (4) Date: Mar. 30, 2001

(87) PCT Pub. No.: WO00/20421
PCT Pub. Date: Apr. 13, 2000

(30) Foreign Application Priority Data

Oct. 6, 1998 (EP) ............................................. 98203370

(51) Int. Cl.⁷ ............... C07D 491/048; C07D 495/04; A61K 31/4355; A61K 31/4365; A61P 25/16
(52) U.S. Cl. ........................ 514/259; 544/319; 544/320; 544/268; 544/284; 544/250; 546/80; 546/89; 514/291; 514/265; 514/267; 514/269
(58) Field of Search ..................... 546/80, 89; 514/291, 514/265, 259, 267, 269; 544/319, 320, 268, 284, 250

(56) References Cited

U.S. PATENT DOCUMENTS 4,740,602 A    4/1988 Bottcher et al. ............ 548/406

6,352,999 B1 * 3/2002 Kennis et al. ............... 514/291

FOREIGN PATENT DOCUMENTS

| EP | 0 206 225 A | 12/1986 |
|---|---|---|
| EP | 1 057 814 | 12/2000 |
| WO | WO89 12447 A | 12/1989 |
| WO | WO99 33804 A | 7/1999 |

OTHER PUBLICATIONS

JC Jaen et al. "Synthesis of the 1,2,3,4–Tetrahydrobenzofuro [2,3–x] Pyridine Ring System", Journal of Heterocyclic Chemistry, vol. 24, No. 24, Sep. 1987, pp. 1317–1319.

* cited by examiner

Primary Examiner—Mark L. Berch
Assistant Examiner—Kahsay Habte
(74) Attorney, Agent, or Firm—Woodcock Washburn LLP

(57) ABSTRACT

The present invention concerns the compounds of formula

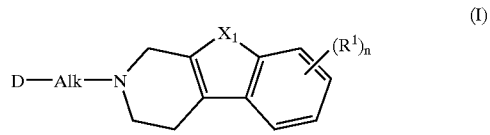

the N-oxide forms, the pharmaceutically acceptable addition salts and the stereochemically isomeric forms thereof, wherein Alk is $C_{1-6}$alkanediyl; n is 1 or 2; $X_1$ is —O—, —S—, —S(=O)— or —S(=O)$_2$—; each $R^1$ is independently hydrogen, halogen, $C_{1-6}$alkyl, nitro, hydroxy or $C_{1-4}$alkyloxy; D is an optionally substituted mono, bi- or tricyclic nitrogen containing heterocycle, a 2H-benzopyranone, a benzamide, a benzophenone or a phenoxyphenyl having central $\alpha_2$-adrenoceptor antagonist activity. It further relates to their preparation, pharmaceutical use and compositions.

11 Claims, No Drawings

TRICYCLIC Δ-3-PIPERIDINES AS α₂-ANTAGONISTS

This application is a National Stage application under 35 U.S.C. §371 of PCT/EP99/07419 filed Oct. 1, 1999, which claims priority from EP 98.203.370.6, filed Oct. 6, 1998.

The present invention concerns tricyclic Δ3-piperidines having central α₂-adrenoceptor antagonist activity. It further relates to their preparation, compositions comprising them and their use as a medicine.

Central α₂-adrenoceptor antagonists are known to increase noradrenaline release by blocking presynaptic α₂-receptors which exert an inhibiting control over the release of the neurotransmitter. By increasing the noradrenaline concentrations, α₂-antagonists can be used clinically for the treatment or prophylaxis of depression, cognitive disturbances, Parkinson's disease, diabetes mellitus, sexual dysfunction and impotence, elevated intraocular pressure, and diseases related to disturbed enterokinesia, since all these conditions are associated with a deficiency of noradrenaline in the central or peripheral nervous system.

The compounds of the present invention are novel and have a specific and selective binding affinity for the different known subtypes of the α₂-adrenoceptors, i.e. the α₂A, α₂B and α₂C-adrenoceptor.

The present invention concerns the compounds of formula

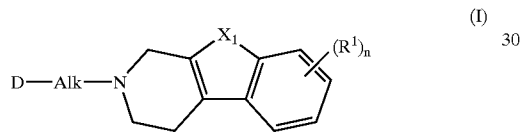
(I)

the N-oxide forms, the pharmaceutically acceptable addition salts and the stereochemically isomeric forms thereof, wherein:

Alk is $C_{1-6}$alkanediyl;
n is 1 or 2;
$X_1$ is —O—, —S—, —S(=O)— or —S(=O)$_2$—;
each $R^1$ is independently hydrogen, halogen, $C_{1-6}$alkyl, nitro, hydroxy or
$C_{1-4}$alkyloxy;
D is a radical of formula

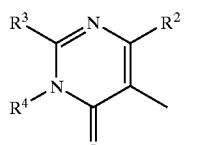
(a)

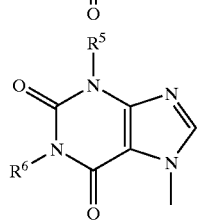
(b)

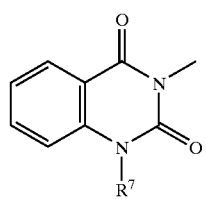
(c)

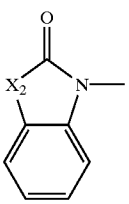
(d)

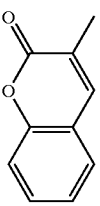
(e)

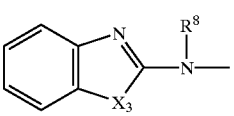
(f)

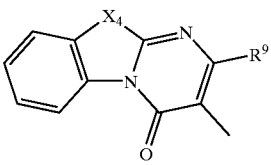
(g)

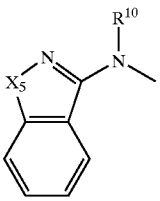
(h)

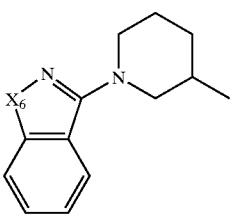
(i)

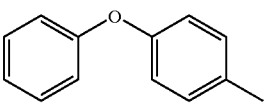
(j)

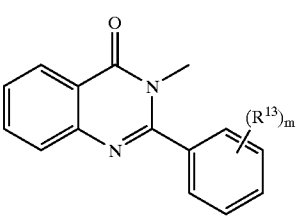
(k)

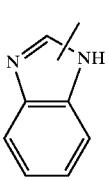
(l)

-continued

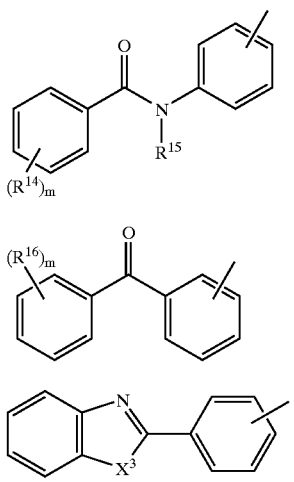

(m)

(n)

(o)

wherein
  each m independently is 0, 1 or 2;
  $X_2$ is —O— or —NR$^{11}$—;
  each $X_3$ independently is —O—, —S— or —NR$^{11}$—;
  $X_4$ is —O—, —S—, —CH$_2$—S— or —NR$^{12}$—;
  $X_5$ and $X_6$ each independently are —CH$_2$—, —O—, —S— or —NR$^{11}$—;
  $R^2$ is hydrogen, $C_{1-6}$alkyl, aryl or aryl$C_{1-6}$alkyl;
  $R^3$ is hydrogen, $C_{1-6}$alkyl, $C_{1-6}$alkyloxy, $C_{1-6}$alkylthio, amino or mono- or di($C_{1-6}$alkyl)amino;
  $R^4$, $R^5$, $R^6$, $R^7$, $R^8$, $R^9$, $R^{10}$, $R^{11}$ and $R^{15}$ each independently are hydrogen or $C_{1-6}$alkyl;
  $R^{12}$ is hydrogen, $C_{1-6}$alkyl, $C_{1-6}$alkyloxy$C_{1-6}$alkyl or pyridinyl$C_{1-6}$alkyl;
  $R^{13}$, $R^{14}$ sand $R^{16}$ each independently are halo or $C_{1-6}$alkyl;
  $R^3$ and $R^4$ taken together may form a bivalent radical —$R^3$—$R^4$— of formula —CH$_2$—CH$_2$—CH$_2$—     (a-1);

—CH$_2$—CH$_2$—CH$_2$—CH$_2$—     (a-2);

—CH=CH—CH$_2$—     (a-3);

—CH$_2$—CH=CH—     (a-4) or

—CH=CH—CH=CH—     (a-5);

wherein one or two hydrogen atoms of said radicals (a-1) to (a-5) each independently may be replaced by halo, $C_{1-6}$alkyl, aryl$C_{1-6}$alkyl, trifluoromethyl, amino, hydroxy, $C_{1-6}$alalkyloxy or $C_{1-10}$alkylcarbonyloxy; or where possible, two geminal hydrogen atoms may be replaced by $C_{1-6}$alalkylidene or aryl$C_{1-6}$alkylidene; or —$R^3$—$R^4$— may also be —S—CH$_2$—CH$_2$—     (a-6);

—S—CH$_2$—CH$_2$—CH$_2$—     (a-7);

—S—CH=CH—     (a-9);

—NH—CH$_2$—CH$_2$—     (a-9);

—NH—CH$_2$—CH$_2$—CH$_2$—     (a-10);

—NH—CH=CH—     (a-11);

—NH—CH=N—     (a-12);

—S—CH=N—     (a-13) or

—CH=CH—O—     (a-14);

wherein one or where possible two or three hydrogen atoms in said radicals (a-6) to (a-14) each independently may be replaced by $C_{1-6}$alkyl or aryl; and aryl is phenyl or phenyl substituted with one, two or three substituents selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl.

As used in the foregoing definitions the term halogen is generic to fluoro, chloro, bromo and iodo. The term $C_{1-4}$alkyl defines straight and branched saturated hydrocarbons, having from 1 to 4 carbon atoms such as, for example, methyl, ethyl, propyl, butyl, 1-methylethyl, 1,1-dimethylethyl, 2-methylpropyl and the like. The term $C_{1-6}$alkyl is meant to include $C_{1-4}$alkyl radicals and the higher homologues thereof having 5 or 6 carbon atoms such as, for example, pentyl, hexyl and the like. The term $C_{1-10}$alkyl is meant to include $C_{1-6}$alkyl radicals and the higher homologues thereof having 7 to 10 carbon atoms such as, for example, heptyl, octyl, nonyl, decyl and the like. The term $C_{1-5}$alkanediyl defines bivalent straight or branch chained alkanediyl radicals having from 1 to 5 carbon atoms such as, for example, methylene, 1,2-ethane-diyl, 1,3-propanediyl, 1,4-butanediyl, 1,5-pentanediyl and the like. $C_{1-6}$alkanediyl is meant to include $C_{1-5}$alkanediyl and the higher homologue thereof havin 6 carbon atoms such as 1,6-hexanediyl and the like. The term $C_{1-6}$alkylidene defines bivalent straight or branch chained alkylidene radicals having from 1 to 6 carbon atoms such as, for example, methylene, ethylidene, 1-propylidene, 1-butylidene, 1-pentylidene, 1-hexylidene and the like.

The addition salts as mentioned herein are meant to comprise the therapeutically active addition salt forms which the compounds of formula (I) are able to form with appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are also meant to comprise the therapeutically active non-toxic base, in particular, a metal or amine addition salt forms which the compounds of formula (I) are able to form. Said salts can conveniently be obtained by treating the compounds of formula (I) containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Conversely said salt forms can be converted by treatment with an appropriate base or acid into the free acid or base form.

The term addition salt as used hereinabove also comprises the solvates which the compounds of formula (I) are able to form and said solvates are meant to be included within the scope of the present invention. Examples of such solvates are, e.g. the hydrates, alcoholates and the like.

The N-oxide forms of the compounds of formula (I) are meant to comprise those compounds of formula (I) wherein one or several nitrogen atoms are oxidized to the so-called N-oxide.

The term stereochemically isomeric forms as used herein defines all the possible isomeric forms in which the compounds of formula (I) may occur. Unless otherwise mentioned or indicated, the chemical designation of compounds denotes the mixture of all possible stereochemically isomeric forms, said mixtures containing all diastereomers and enantiomers of the basic molecular structure.

Some of the compounds of formula (I) may also exist in their tautomeric forms. Such forms although not explicitly indicated in the above formula are intended to be included within the scope of the present invention.

As used hereinafter, when the position of the $R^1$ substitutent is referred to, the following numbering is used:

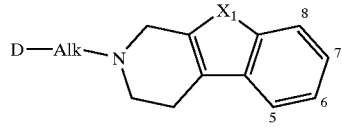

Whenever used hereinafter, the term compounds of formula (I) is meant to include also the N-oxide forms, the pharmaceutically acceptable addition salts and all stereoisomeric forms.

Special compounds are those compounds of formula (I) wherein D is a radical of formula (a), (b), (c), (d), (e), (f), (g), (h), (i), (j), (k) or (l); m is 0; and aryl is phenyl or phenyl substituted with halo or $C_{1-6}$alkyl.

An interesting group of compounds are those compounds of formula (I) wherein n is 1 and $R^1$ is hydrogen, chloro, fluoro, methyl, methoxy or nitro, in particular $R^1$ is hydrogen, chloro, fluoro, methyl or methoxy.

In case $R^1$ is other than hydrogen, then $R^1$ is suitably connected to the tricyclic ring system in the 6 or 7 position.

Another interesting group of compounds are those compounds of formula (I) wherein Alk is methylene, 1,2-ethanediyl, 1,3-propanediyl, 1,4-butanediyl or 1,5-pentanediyl.

Still another interesting group of compounds are those compounds of formula (I) wherein D is a radical of formula (a) wherein $R^2$ is aryl or methyl and wherein $R^3$ and $R^4$ are taken together to form a bivalent radical of formula (a-5) or (a-8); or D is a radical of formula (b) wherein $R^5$ and $R^6$ are $C_{1-6}$alkyl, preferably $R^5$ and $R^6$ are methyl; or D is a radical of formula (c) wherein $R^7$ is hydrogen; or D is a radical of formula (d) wherein $X_2$ is —$NR^{11}$— and $R^{11}$ is hydrogen; or D is a radical of formula (e); or D is a radical of formula (f) wherein $X_3$ is —S— and $R^8$ is hydrogen or $C_{1-6}$alkyl, preferably $R^8$ is methyl; or D is a radical of formula (g) wherein $X_4$ is —$CH_2$—S— or —$NR^{12}$— and $R^{12}$ is $C_{1-6}$alkyloxy$C_{1-6}$alkyl or pyridinyl$C_{1-6}$alkyl, preferable $R^{12}$ is ethyloxyethyl or pyridinylmethyl; or D is a radical of formula (h) wherein $X_5$ is —O— or —S— and $R^{10}$ is hydrogen; or D is a radical of formula (); or D is a radical of formula (k) wherein m is preferably 1 and $R^{13}$ is halo.

Particular compounds are those compounds of formula (I) wherein n is $X_1$ is —O— or —S—.

Preferred compounds are those compounds of formula (I) wherein n is 1, $R^1$ is hydrogen, chloro, fluoro, methoxy or methyl, $X_1$ is —O— or —S— and D is a radical of formula (a), (b), (c), (d), (e), (f), (g), (h), (j) or (k).

More preferred compounds are those compounds of formula (I) wherein D is a radical of formula (a), (c), (d), (f) and (h); $X_1$ is O or S; n is 1; $R^1$ is hydrogen, halo or methyl and is substituted in the 6 position; and Alk is 1,2-ethanediyl, 1,3-propanediyl or 1,4-butanediyl.

Most preferred compounds are the compounds depicted below or their N-oxide forms, the pharmaceutically acceptable addition salts and the stereochemically isomeric forms thereof:

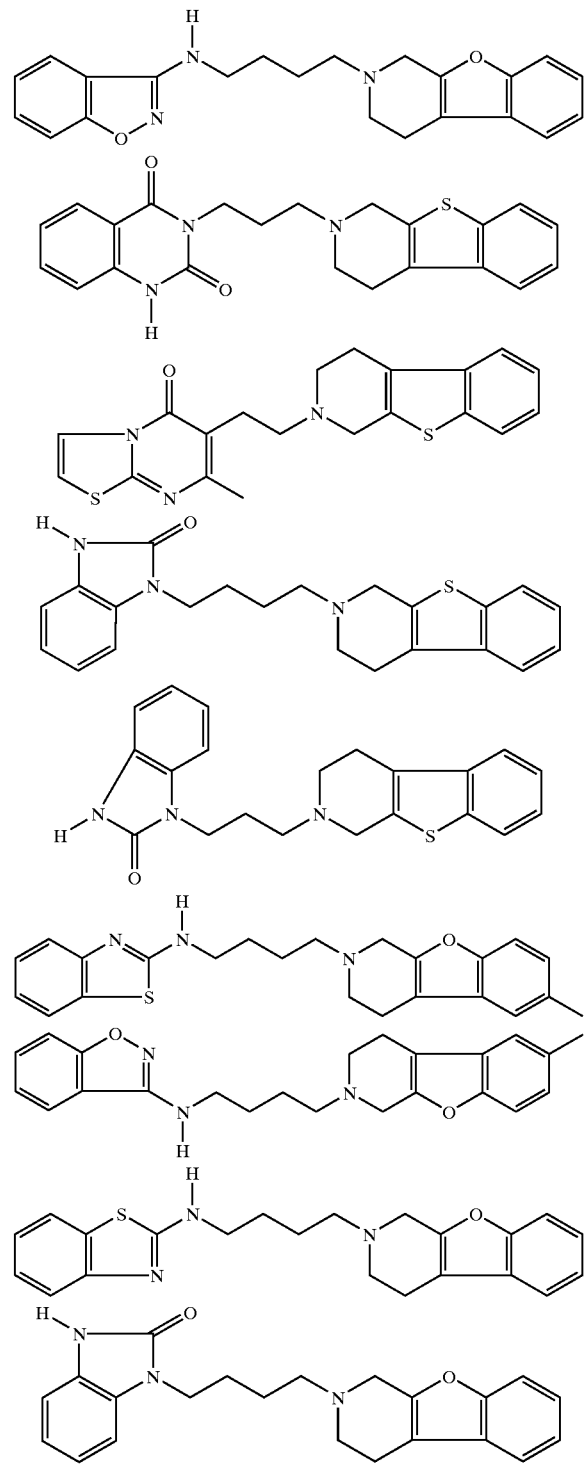

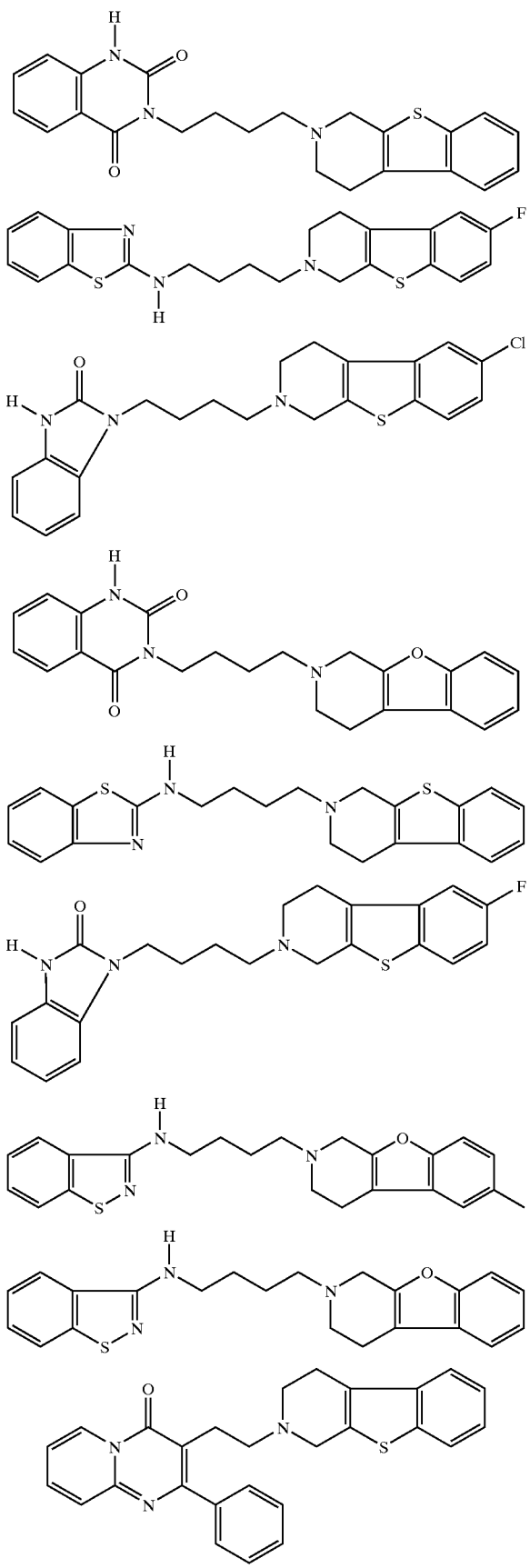

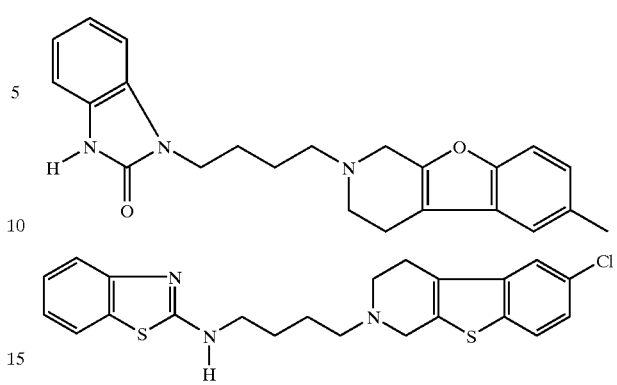

The compounds of formula (I) can generally be prepared by N-alkylating an intermediate of formula (II) with an alkylating reagent of formula (II) following the procedure described in EP-A-0,037,265, EP-A-0,070,053, EP-A-0,196,132 and in EP-A-0,378,255. In particular, the N-alkylation may be performed in a reaction-inert solvent such as, methyl isobutyl keton, N,N-dimethylformamide or N,N-dimethyl-acetamide, in the presence of a base, for example, triethylamine, sodium carbonate or sodiumbicarbonate, and optionally in the presence of a catalyst such as potassium iodide.

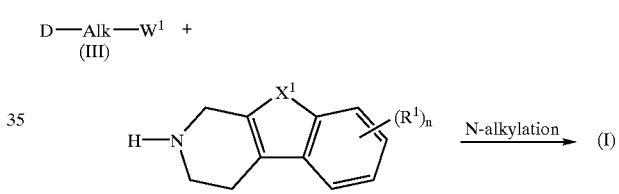

In intermediate (III), $W^1$ represents an appropriate reactive leaving group such as, halo, e.g. chloro, bromo or iodo; sulfonyloxy, e.g. methanesulfonyloxy, 4-methyl-benzenesulfonyloxy.

In this and the following reactions, the reaction products may be isolated from the reaction medium and, if necessary, further purified according to methodologies generally known in the art such as extraction, crystallization, trituration and chromatography.

The compounds of formula (I) wherein D is a radical of formula (f), being represented by formula (I-f), can be prepared by N-alkylating an amine of formula (IV) with an intermediate of formula (V) wherein $W^2$ is an appropriate reactive leaving group such as, for example, a halogen.

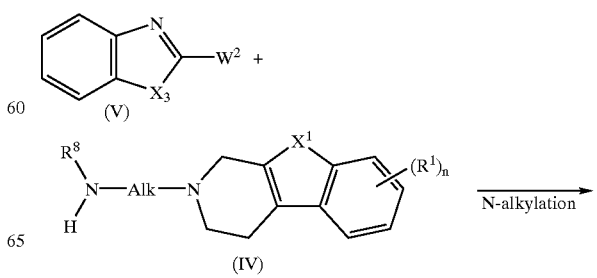

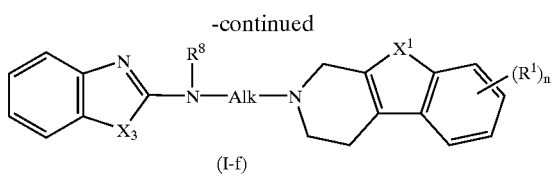

(I-f)

A specific way of preparing the compounds of formula (I) wherein D is a radical of formula (j) and Alk is —(Alk')$_p$—CH$_2$— wherein Alk' is C$_{1-5}$alkanediyl and p is 0 or 1, said compounds being represented by formula (I-j), involves the reductive N-alkylation of an intermediate of formula (II) with an aldehyde derivative of formula (VI).

The compounds of formula (I) may be converted into each other following art-known functional group transformation reactions.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substtituted benzenecarboper-

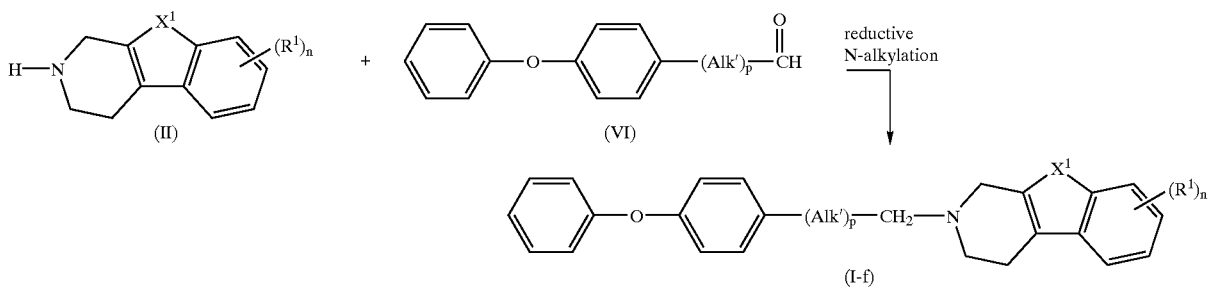

Said reductive N-alkylation reaction may conveniently be carried out by reducing a mixture of the reactants in a suitable reaction-inert solvent following art-known reductive N-alkylation procedures. In particular, the reaction mixture maybe stirred and/or heated in order to enhance the reaction rate. Suitable solvents are, for example, water; methanol, ethanol, 2-propanol and the like. The reaction is conveniently carried out either with sodium cyanoborohydride, sodium borohydride, formic acid or a salt thereof and the like reducing agents, or alternatively under hydrogen atmosphere, optionally at an increased temperature and/or pressure, in the presence of an appropriate catalyst such as, for example, palladium-on-charcoal, platinum-on-charcoal and the like. In order to prevent the undesired further hydrogenation of certain functional groups in the reactants and the reaction products, it may be advantageous to add an appropriate catalyst-poison to the reaction mixture, e.g., thiophene, quinoline-sulphur and the like. In some instances it may also be advantageous to add an alkali metal salt to the reaction mixture such as, for example, potassium fluoride, potassium acetate and the like salts.

oxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

A number of intermediates and starting materials are commercially available or are known compounds which may be prepared according to art-known methodologies.

For example, some of the intermediates of formula (III) and their preparations are described in EP-A-0,037,265, EP-A-0,070,053, EP-A-0,196,132 and in EP-A-0,378,255.

Intermediates of formula (II) wherein X$_1$ is —O— can be prepared as described in Syn. Comm. (1995), p3883–3900 and J. Chem. Soc., 1965, p4939–4953 and using methods known in the art. A general procedure is depicted in scheme 1.

Intermediates of formula (II) wherein X$_1$ is —S— can be prepared according to J. Med. Chem., 1992, 35(7), p1176–1182 and using methods known in the art. A general procedure is depicted in scheme 2.

Scheme 2

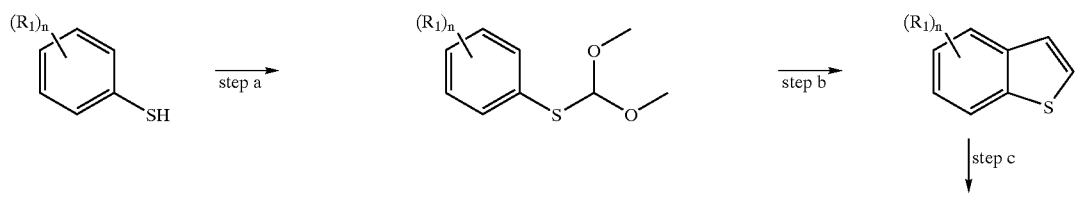

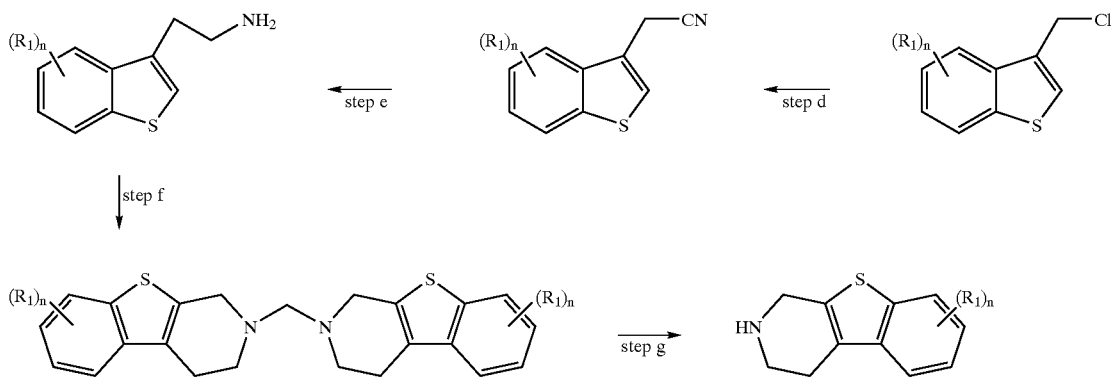

Alternatively, intermediates of formula (II) can be prepared according to Synth. Comm., 1995, p3883–3900 and using methods known in the art. A general procedure is depicted in scheme 3.

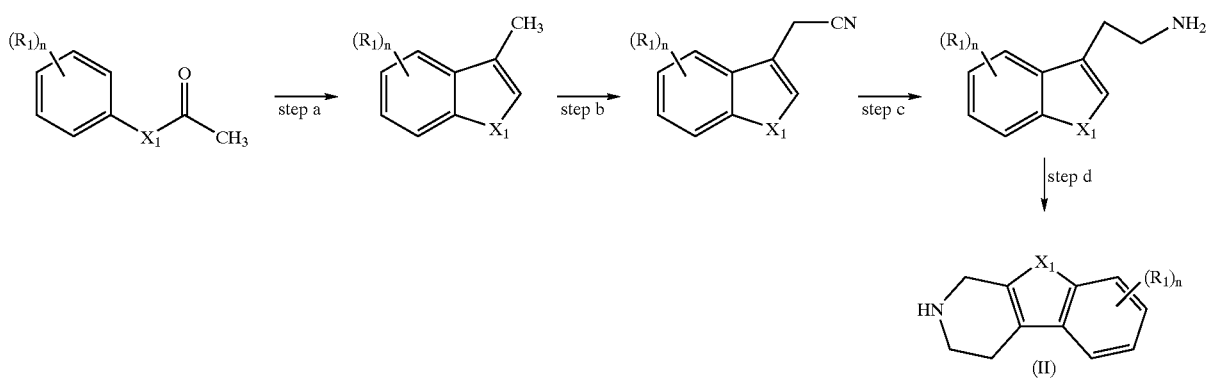

Intermediates of formula (III) wherein D is a radical of formula (h), said intermediates being represented by formula (III-h), can be prepared by reacting a benzisoxazole or benzisothiazole of formula (VI) wherein $W^3$ is a suitable leaving group such as, a halogen, with an amino-alcohol derivative of formula (VIII) in the presence of a catalyst such as, potassium iodide. Conveniently, the reaction mixture is stirred at elevated temperatures. Subsequently, a suitable leaving group such as, a halogen, e.g. chloro, can be introduced in the thus formed alcohol derivative using art-known techniques, for instance, reacting the alcohol with thionylchloride in a solvent such as chloroform.

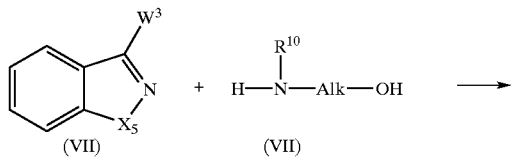

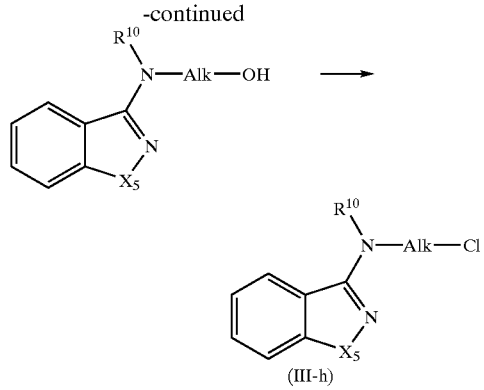

Some of the compounds of formula (I) and some of the intermediates in the present invention contain at least one asymmetric carbon atom. Pure stereo chemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers.

Pure stereochemically isomeric forms of the compounds of formula (I) may also be obtained from the pure stereochemically isomeric forms of the appropriate intermediates and starting materials, provided that the intervening reactions occur stereospecifically. The pure and mixed stereochemically isomeric forms of the compounds of formula (I) are intended to be embraced within the scope of the present invention.

The compounds of formula (I), the N-oxides, the pharmaceutically acceptable addition salts and stereochemically isomeric forms thereof, block the presynaptic $\alpha_2$-receptors on central noradrenergic neurons thus increasing the noradrenaline release. Blocking said receptors will suppress or relieve a variety of symptoms associated with a deficiency of noradrenaline in the central or peripheral nervous system. Therapeutic indications for using the present compounds are depression, cognitive disturbances, Parkinson's disease, diabetes mellitus, sexual dysfunction and impotence and elevated intraocular pressure.

Blocking $\alpha_2$ receptors in the central nervous system has also been shown to enhance the release of serotonine which may add to the therapeutic action in depression (Maura et al., 1992, Naunyn-Schmiedeberg's Arch. Pharmacol., 345:410–416).

It has also been shown that blocking $\alpha_2$ receptors may induce an increase of extracellular DOPAC (3,4-dihydrophenylacetic acid) which is a metabolite of dopamine and noradrenaline.

In view of the usefulness of the subject compounds in the treatment of diseases associated with a deficiency of noradrenaline in the central nervous system, in particular depression and Parkinson's disease, the present invention provides a method of treating warm-blooded animals suffering from such diseases, in particular depression and Parkinson's disease, said method comprising the systemic administration of an therapeutically effective amount of a compound of formula (I) or a pharmaceutically acceptable addition salt thereof.

The present compounds are also potentially useful in the treatment of Alzheimer's disease and dementia as it is known that $\alpha_2$-antagonists promote the release of acetylcholine (Tellez et al. 1997, J. Neurochem. 68:778–785).

In general it is contemplated that an effective therapeutic daily amount would be from about 0.01 mg/kg to about 4 mg/kg body weight.

The present invention thus also relates to compounds of formula (I) as defined hereinabove for use as a medicine. Further, the present invention also relates to the use of a compound of formula (I) for the manufacture of a medicament for treating depression or Parkinson's disease.

Ex vivo as well as in vitro receptor signal-transduction and receptor binding studies can be used to evaluate the $\alpha_2$ adrenoceptor antagonism of the present compounds. As indices of central ($\alpha_2$-adrenoceptor blockade in vivo, the reversal of the loss of righting reflex observed in rats after intravenous injection of xylazine and inhibition of the tremors induced by reserpine in rats can be used.

The compounds of the present invention also have the ability to rapidly penetrate into the central nervous system.

For administration purposes, the subject compounds may be formulated into various pharmaceutical compositions comprising a pharmaceutically acceptable carrier and, as active ingredient, a therapeutically effective amount of a compound of formula (I). To prepare the pharmaceutical compositions of this invention, an effective amount of the particular compound, in addition salt or in free acid or base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Addition salts of (I) due to their increased water solubility over the corresponding free base or free acid form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate the present invention.

EXPERIMENTAL PART

Hereinafter, the term 'RT' means room temperature, 'THF' means tetrahydrofuran and 'DIPE' means diisopropylether.

A. Preparation of the Intermediate Compounds

EXAMPLE A1 a) A mixture of 3-chloro-1,2-benzisoxazole (0.08 mol), 4-amino-1-butanol (0.24 mol) and KI (1 g) was stirred for 4 days at 80° C. The reaction mixture was cooled, dissolved in $CH_2Cl_2$ and purified by column chromatography over silica gel (eluent: $CH_2Cl_2/CH_3OH$ 95/5). The pure fractions were collected and the solvent was evaporated, yielding 15.4 g (93%) of 4-(1,2-benzisoxazol-3-ylamino)-1-butanol (interm. 1). b) Thionyl chloride (0.048 mol) was cooled to 0° C. A solution of intermediate (1) (0.048 mol) in $CHCl_3$ (20 ml) was added dropwise and the reaction mixture was stirred overnight at RT. The solvent was evaporated. The residue was washed with water. The reaction mixture was extracted with $CH_2Cl_2$. The separated organic layer was dried ($MgSO_4$), filtered, and the solvent was evaporated, yielding 10.4 g of ON—(4-chloro-butyl)-1,2-benzisoxazol-3-amine (interm. 2).

EXAMPLE A2 a) Reaction under $N_2$ atmosphere. NaH 60% (0.17 mol) was stirred in TBF (350 ml). A solution of diethyl (cyanomethyl)phosphonate (0.17 mol) in THF (150 ml) was added dropwise over ±20 minutes. (exothermic temperature rise to 30° C.). The mixture was stirred for 20 minutes at RT, then cooled to 0° C. A solution of 5-methyl-3-benzofuranone (0.15 mol) in THF (350 ml) was added dropwise over 30 minutes at 0° C. reaction mixture was stirred overnight at RT, then poured out into water (1500 ml) and stirred. This mixture was extracted with ether, DIPE (2×), dried ($MgSO_4$), filtered and the solvent was evaporated. The residue was purified by column chromatography over silica gel (eluent: $CH_2Cl_2$/hexane 50/50). The desired fractions were collected and the solvent was evaporated, yielding 21.2 g (82%) of 5-methyl-3-benzofuranacetonitrile (interm. 3).

b) A mixture of intermediate (3) (0.12 mol) in $NH_3/CH_3OH$ (400 ml) was hydrogenated with Raney Nickel (3 g) as a catalyst. After uptake of $H_2$ (2 equiv), the catalyst was filtered off and the filtrate was evaporated. The residue was purified over silica gel on a glass filter (eluent: $CH_2Cl_2/(CH_3OH/NH_3)$ 98/2 to 96/4). The desired fractions were collected and the solvent was evaporated. The residue (±2.1 g) was dissolved in 2-propanol (500 ml), and converted into the hydrochloric acid salt (1:1) with HCl/2-propanol. The mixture was stirred at RT. The solvent was evaporated. The residue was stirred in DIPE, filtered off and dried, yielding 24.4 g (96%) of 5-methyl-3-benzofuranethanamine hydrochloride (1:1)(interm. 4).

c) A mixture of intermediate (4) (0.0024 mol) in $H_2O$ (2 ml), acetic acid (2 ml) and formal 37% (2 ml) was stirred for one hour at 100° C. The reaction mixture was cooled and poured out into 1 M NaOH (50 ml). The precipitate was filtered off, washed with water, then dissolved in 1 N HCl (100 ml). The mixture was stirred for 15 minutes on a warm-water-bath (80° C.). The solvent was evaporated. 2-Propanol was added. The solvent was evaporated. The residue was stirred in boiling 2-propanone, then allowed to cool to RT while stirring. The precipitate was filtered off and dried, yielding 0.40 g of 1,2,3,4-tetrahydro-6-methylbenzofuro[2,3-c]pyridine monohydrochloride.monohydrate (interm. 5).

EXAMPLE A3 a) A mixture of 1,2,3,4-tetrahydro-[1]benzothieno[2,3-c]pyridine (0.02 mol), $Na_2CO_3$ (5 g), KI (0.1 g) and 4-chlorobutanenitrile (0.025 mol) in acetonitrile (50 ml) and methylbenzene (150 ml) was stirred and refluxed overnight, then cooled, filtered and the filtrate was evaporated. The residue (oil) was purified by column chromatography over silica gel (eluent: $CH_2Cl_2/CH_3OH$ 98/2). The pure fractions were collected and the solvent was evaporated, yielding 5.2 g of 3,4-dihydrobenzothieno[2,3-c]-pyridine-2(1H)-butanenitrile (interm. 6).

b) A mixture of intermediate (6) (0.0195 mol) in $NH_3/CH_3OH$ (200 ml) was hydrogenated with Raney Nickel (4 g) as a catalyst in the presence of thiophene solution (4 ml). After uptake of $H_2$ (2 equiv), the catalyst was filtered off over dicalite and the filtrate was evaporated, yielding 3.9 g of 3,4-dihydrobenzothieno[2,3-c]-pyridine-2(1H)-butanamine (interm. 7).

EXAMPLE A4 a) A mixture of 6-chloro-1,2,3,4-tetrahydro[1]benzothieno[2,3-c]pyridine (0.02 mol), 1,1-dimethylethyl (4-chlorobutyl)carbamate (0.02 mol), $Na_2CO_3$ (3.5 g) and KI (0.1 g) in 4-methyl-2-pentanone (300 ml) was stirred and refluxed overnight. The reaction mixture was cooled, filtered and the filtrate was evaporated. The residue was purified by column chromatography over silica gel (eluent: $CH_2Cl_2/CH_3OH$ 96/4). The desired fractions were collected and the solvent was evaporated, yielding 5.2 g of 1,1-dimethylethyl [4-(6-chloro-3,4-dihydrobenzo[1]thieno-[2,3-c]pryridine-2 (1H )-yl)-butyl]carbamate (interm. 8).

b ) A mixture of intermediate (8) (0.013 mol) in HCl/2-propanol (50 ml) and 2-propanol (100 ml) was stirred and refluxed for 30 min. The reaction mixture was cooled. The precipitate (.HCl salt) was filtered off and converted into the free base with $NH_4OH$. This mixture was extracted with $CH_2Cl_2$. The separated organic layer was dried, filtered and the solvent evaporated. The residue was triturated under $CH_3CN/DIPE$, filtered off and dried, yielding 2.2 g of 6-chloro-3,4-dihydrobenzo[1]thieno-[2,3-c]pyridine-2(1H)-butanamine (interm. 9).

EXAMPLE A5 a) A mixture of formaldehyde 37% (31 g) and $ZnCl_2$ (10 g) in ethyl acetate (90 ml) and HCl 12N (190 ml) was stirred at −10° C. HCl (gas) was allowed to bubble through the mixture until saturation (at −10° C.). 5-fluorobenzo[b]thiophene (0.35 mol) was added dropwise at <0° C. The reaction mixture was stirred overnight at room temperature. Toluene (200 ml) was added and the mixture was stirred vigorously. The organic layer was separated, washed with an aqueous $NaHCO_3$ solution and with water, dried, filtered and the solvent was evaporated. The residue was triturated under hexane, filtered off and dried, yielding 58 g of 3-(chloromethyl)-5-fluorobenzo[b]thiophene (82.6%) (interm. 10).

b) A mixture of sodium cyanide (0.33 mol) and octahydrodibenzo[b,k][1,4,7,10,13,16]-hexaoxacyclooctadecin (0.050 g) in dimethylsulfoxide (110 ml) was stirred at 30° C. Intermediate (10) (0.29 mol) was added over a 30-min period. The mixture was allowed to cool to room temperature while stirring. Then, the reaction mixture was stirred in ice-water. The precipitate was filtered off, washed with water, then dissolved in $CH_2Cl_2$. The organic solution was dried, filtered and the solvent was evaporated, yielding 5-fluorobenzo[b]thiophene-3-acetonitrile (interm. 11).

c) A mixture of intermediate (11) (0.29 mol) in $NH_3/CH_3OH$ (700 ml) was hydrogenated at 14° C. with Raney Nickel (5 g) as a catalyst in the presence of a thiophene solution (10 ml). After uptake of $H_2$ (2 equiv), the catalyst was filtered off over dicalite and the filtrate was evaporated. The residue was purified by column chromatography over silica gel (eluent: $CH_2Cl_2/(CH_3OH/NH_3)$ 96/4). The desired fractions were collected and the solvent was evaporated. The residue was dissolved in DIPE and converted into the hydrochloric acid salt (1:1) with HCl/2-propanol. The precipitate was filtered off, washed with DIPE, and dried, yielding 48.5 g of 5-fluorobenzo[b]thiophene-3-ethanamine hydrochloride(1:1) (interm. 12).

d) A mixture of intermediate (12) (0.21 mol) in $H_2O$ (190 ml), acetic acid (190 ml) and formaldehyde, 37% (190 ml) was stirred and refluxed for one hour. The mixture was allowed to cool to room temperature, then poured out in NaOH 4N (1200 ml), while stirring. The precipitate was filtered off and triturated under $CH_3CN$, filtered off, washed with DIPE and dried yielding 21 g of 1,1'-methylenebis[6-fluoro-1,2,3,4-tetrahydro-[1]benzothieno[2,3-c]pyridine (interm. 13).

e) A mixture of intermediate (13) (0.049 mol) in water (1700 ml) and HCl 12N (285 ml) was stirred and refluxed for one hour. The precipitate was filtered off, washed with $CH_3CN$ and DIPE, and dried, yielding 17.7 g of 6-fluoro-1,2,3,4-tetrahydro-[1]benzothieno[2,3-c]pyridine hydrochloride (interm. 14)

EXAMPLE A6

Reaction under $N_2$ atmosphere. A solution of 1,2-dichloro ethanedioyl (0.026 mol) in $CH_2Cl_2$ (60 ml) was stirred at −60° C. Dimethylsulfoxide (3.8 ml) was added dropwise at −60° C. and the mixture was stirred for 10 min. A solution of intermediate (1) (0.024 mol) in $CH_2Cl_2$ (120 ml) was added dropwise at −60° C. and the mixture was stirred for one hour at −60° C. N,N-diethylethanamine (13.7 ml) was added dropwise and the reaction mixture was stirred for 10 min at −60° C., then allowed to warm to room temperature. The mixture was poured out into water (250 ml). The mixture was stirred for 10 min. The separated organic layer was dried, filtered and the solvent evaporated. The residue was triturated under hexane, filtered off and dried, yielding 3.9 g of 4-(1,2-benzisoxazol-3-ylamino)butanal (80%) (interm. 15).

B. Preparation of the Final Compounds

EXAMPLE B1

A mixture of 1,2,3,4-tetrahydro-benzofuro[2,3-c]pyridine hydrochloride (1:1) (0.007 mol), 3-(2-chloroethyl)-2-methyl-4H-pyrido[1,2-a]pyrimidin-4-one(0.012 mol), $Na_2CO_3$ (0.015 mol) and KI (catalytic quantity) in 2-butanone (100 ml) was stirred and refluxed overnight. The reaction mixture was filtered hot and the filtrate was evaporated. The residue was purified by column chromatography over silica gel (eluent: $CH_2Cl_2/(CH_3OH/NH_3)$ from 98/2 to 97/3). The purest fractions were collected and the solvent was evaporated. The residue was dissolved in 2-propanol and (E)-2-butenedioic acid (1 g) was added. The mixture was boiled and then stirred at RT. The precipitate was filtered off and dried, yielding 2.00 g (61%) of 3-[2-(3,4-dihydro-benzofuro[2,3-c]pyridin-2(1H)-yl)ethyl]-2-methyl-4H-pyrido[1,2-a]pyrimidin-4-one (E)-2-butenedioate (2:1) (compound 1).

EXAMPLE B1b

A mixture of 6-chloro-1,2,3,4-tetrahydro-[1]benzothieno [2,3-c]pyridine hydrochloride (1:1) (0.01 mol), 1-(4-chlorobutyl)-1,3-dihydro-3-(1-methylethenyl)-2H-benzimidazol-2-one (0.01 mol), $Na_2CO_3$ (3.5 g) and KI (0.1 g) in 2-butanone (200 ml) was stirred and refluxed overnight, then cooled, filtered and the filtrate was evaporated. The residue was purified by column chromatography over silica gel (eluent: $CH_2Cl_2/(CH_3OH/NH_3)$ 95/5). The desired fractions were collected and the solvent was evaporated. The residue was stirred in boiling HCl/2-propanol. DIPE was added and the mixture was stirred. The precipitate was filtered off, washed with DIPE and dried. This fraction was converted into the free base, then extracted with $CH_2Cl_2$. The separated organic layer was dried, filtered and the solvent evaporated. The residue was dissolved in 2-propanone and converted into the (E)-2-butenedioic acid salt (1:1). The precipitate was filtered off, washed with DIPE, and dried, yielding 0.82 g of 1-[4-(6-chloro-3,4-dihydroenzothieno[2,3-c]pyridin-2(1H)-yl)butyl]-1,3-dihydro-2H-benzimidazol-2-one (E)-2-butenedioate (1:1) (compound 21).

EXAMPLE B2

A mixture of 1,2,3,4-tetrahydro-[1]benzothieno[2,3-c] pyridine hydrochloride (1:1) (0.00057 mol), 7-(2-chloroethyl)-1,3-dimethyl-7H-purine-2,6-(1H,3H)-dione (0.100 g) and $Na_2CO_3$ (0.100 g) in 2-butanone (2 ml) was stirred over the weekend at 100° C. The desired compound was isolated and purified by high-performance liquid chromato-graphy over Kromasil Spherical underivated silica gel (55 g, 60 Å, 5 μm) (column: 2 cm I.D.; eluent: $CH_2Cl_2/ (CH_2Cl_2/CH_3OH$ 90/10)/$CH_3OH$ (0 minutes) 100/0/0, (10.50 minutes) 0/100/0, (12.50 minutes) 50/0/50, (14.00 minutes) 0/0/100, (15.01–20.00 minutes) 100/0/0). The pure fractions were collected and the solvent was evaporated, yielding 0.070 g of 7-[2-(3,4-dihydrobenzothieno[2,3-c] pyridin-2(1H)-yl)ethyl]-1,3-dimethyl-1H-purine-2,6(3H, 7H)-dione (compound 7).

EXAMPLE B3

A mixture of intermediate (9) (0.007 mol), 2-chlorobenzothiazole (0.01 mol) and $Na_2CO_3$ (2 g) in 2-ethoxyethanol (50 ml) was stirred and refluxed for 3 hours. The reaction mixture was cooled, filtered and the filtrate was evaporated. The residue was purified by column chromatography over silica gel (eluent: $CH_2Cl_2/CH_3OH$ 96/4). The pure fractions were collected and the solvent was evaporated. The residue was triturated under DIPE/$CH_3CN$, filtered off, washed with DIPE and dried, yielding 1.75 g of N-2-benzothiazolyl-6-chloro-3,4-dihydro-benzo[1]thieno[2, 3-c]pyridine-2(1H)-butanamine (58.3%) (compound 64).

EXAMPLE B4

A mixture of 3,4-dihydro-7-methoxybenzofuro[2,3-c] pyridine-2(1H)-butanamine (0.0055 mol), 3-chloro-1,2-benzisothiazole (0.0089 mol) and $NaHCO_3$ (0.01 mol) was stirred for 1.5 hour at 120° C. (melt). 1-Butanol (0.5 ml) was added. The reaction mixture was cooled, then dissolved in $CH_2Cl_2$ and purified by column chromatography over silica gel (eluent: $CH_2Cl_2/(CH_3OH/NH_3)$ 98/2). The desired fractions were collected and the solvent was evaporated. The residue was dissolved in 2-propanone and converted into the hydrochloric acid salt (1:2) with HCl/2-propanol. The mixture was stirred at room temperature. The precipitate was filtered off and dried, yielding 1.60 g of N-(1,2-benzisothiazol-3-yl)-3,4-dihydro-7-methoxybenzofuro[2,3-c]pyridine-2(1H)-butanamine monohydrochloride monohydrate (61%) (compound 55).

EXAMPLE B5

Acetic acid (0.005 mol) was added to 1,2,3,4-tetrahydro-7-methoxybenzofuro[2,3-c]pyridine hydrochloride monohydrate (0.005 mol) in 1,2-dichloroethane (30 ml). Intermediate (15) (0.005 mol) was added and the mixture was stirred until complete dissolution. $NaBH(OAc)_3$ (0.005 mol) was added and the reaction mixture was stirred over the weekend at room temperature. The reaction mixture was diluted with $CH_2Cl_2$ (100 ml), washed with a 10% aqueous NaOH solution, then dried (MgSO$_4$), filtered and the solvent evaporated. The residue was purified by column chromatography over silica gel (eluent: CH$_2$Cl$_2$/(CH$_3$OH/NH$_3$) 98/2). The desired fractions were collected and the solvent was evaporated. The residue was dissolved in 2-propanone and converted into the (E)-2-butenedioic acid salt (2:1) with (E)-2-butenedioic acid (0.8 g). The mixture was boiled, then allowed to cool to room temperature while stirring. The precipitate was filtered off and dried, yielding 1.50 g of N-(1,2-benzisoxazol-3-yl)-3,4-dihydro-7-methoxybenzofuro[2,3-c]pyridine-2(1H)-butanamine (68%) (compound 65).

EXAMPLE B6

A mixture of intermediate (7) (0.015 mol), 2-chlorobenzothiazole (0.015 mol), Na$_2$CO$_3$ (3 g) and KI (catalytic quantity) in methylbenzene (150 ml) was stirred and refluxed overnight, then cooled to 50° C. The reaction mixture was filtered and the filtrate was evaporated. The residue was purified by column chromatography over silica gel (eluent: CH$_2$Cl$_2$/CH$_3$OH 95/5). The pure fractions were collected and the solvent was evaporated. The residue was crystallized from CH$_3$CN, filtered off and dried, yielding 2.4 g of N-2-benzothiazolyl-3,4-dihydrobenzothieno[2,3-c]pyridine-2(1H)-butanamine (compound 25).

EXAMPLE B7

1,2,3,4-tetrahydrobenzofuro[2,3-c]pyridine hydrochloride (1:1) (0.01 mol) was converted into its free base with CH$_2$Cl$_2$/H$_2$O.NH$_4$OH. A mixture of said free base, intermediate (2) (0.019 mol) and triethylamine (0.015 mol) in N,N-dimethylacetamide (50 ml) was stirred at 70° C. for 48 hours. The solvent was evaporated. The residue was purified by column chromatography over silica gel (eluent: CH$_2$Cl$_2$/(CH$_3$OH/NH$_3$) 98/2). The desired fractions were collected and the solvent was evaporated. The residue was dissolved in 2-propanol and treated with (E)-2-butenedioic acid (1 g). The mixture was boiled, then stirred at RT. The solvent was evaporated. The residue was dissolved in 2-propanone, boiled and then stirred at RT. The solvent was evaporated. The residue was dissolved in 2-propanol, acidified with HCl/2-propanol, stirred and the resulting precipitate was filtered off and dried, yielding 0.70 g (16%) of N-1,2-benzisoxazol-3-yl-3,4-dihydrobenzofuro[2,3-c]pyridin-2(1H)-butanamine monohydrochloride (compound 36)

EXAMPLE B8

Starting material 1,2,3,4-tetrahydrobenzofuro[2,3-c]pyridine hydrochloride (1:1) (0.01 mol) was alkalized, extracted and the solvent evaporated, to give the free base (1.4 g, 0.008 mol). A mixture of said free base and 4-phenoxybenzaldehyde (0.01 mol) in methanol (150 ml) was hydrogenated with Pd/C 10% (1 g) as a catalyst in the presence of thiophene 4% (1 ml). After uptake of H$_2$ (1 equiv), the catalyst was filtered off and the filtrate was evaporated. The residue was purified by column chromatography over silica gel (eluent: CH$_2$/Cl$_2$/(CH$_3$OH/NH$_3$) 98/2). The desired fraction were collected and the solvent was evaporated. The residue was dissolved in 2-propanol and converted into the (E)-2-butenedioic acid salt (1:1) with (E)-2-butenedioic acid (1.2 g). The mixture was boiled, then allowed to cool to RT while stirring. The precipitate was filtered off and dried, yielding 1.80 g (49%) of 1,2,3,4-tetrahydro-2-[(4-phenoxy-phenyl)methyl]benzofuro[2,3-c]pyridine (E)-2-butenedioate (1:1) (compound 33)

EXAMPLE B9

A mixture of 1,2,3,4-tetrahydro-[1]benzothieno[2,3-c]pyridine hydrochloride (1:1) (0.01 mol) and phenoxybenzaldehyde (0.01 mol) in methanol (150 ml) was hydrogenated at 50° C. with Pd/C 10% (1 g) as a catalyst in the presence of potassium acetate (2 g) and thiophene 4% (1 ml). After uptake of H$_2$ (1 equiv), the catalyst was filtered off and the filtrate was evaporated. The residue was crystallized from CH$_3$CN, filtered off and dried. This fraction (3 g) was stirred in water with a little NH$_4$OH, and this mixture was extracted with CH$_2$Cl$_2$. The separated organic layer was dried (MgSO$_4$), filtered and the solvent evaporated. The residue was crystallized from CH$_3$CN, filtered off and dried, yielding 2.7 g of 1,2,3,4-tetrahydro-2-[(4-phenoxy-phenyl)methyl]benzothieno[2,3-c]pyridine (compound 34).

TABLE 1 lists compounds of formula (I) which were prepared according to one of the above examples.

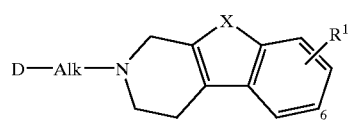

| Co. No. | Ex. No. | R$^1$ | X$_1$ | Alk | D | Salt form |
|---|---|---|---|---|---|---|
| 1 | B1 | H | O | (CH$_2$)$_2$ | 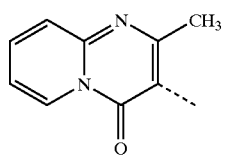 | (E)-2-butenedioate (2:1) |

TABLE 1-continued
lists compounds of formula (I) which were prepared according to one of the above examples.
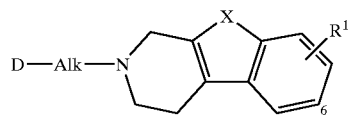
| Co. No. | Ex. No. | R[1] | X[1] | Alk | D | Salt form |
|---|---|---|---|---|---|---|
| 2 | B1 | H | O | (CH$_2$)$_3$ | 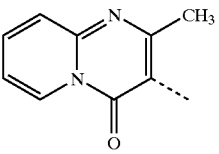 | (E)-2-butenedioate (1:1) |
| 3 | B1 | H | O | (CH$_2$)$_2$ | 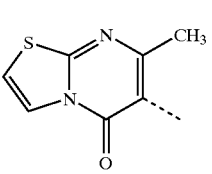 | (E)-2-butenedioate (2:1) |
| 4 | B1 | H | S | (CH$_2$)$_2$ | 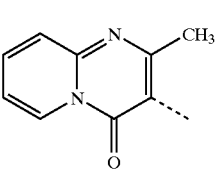 | |
| 5 | B1 | H | S | (CH$_2$)$_2$ | 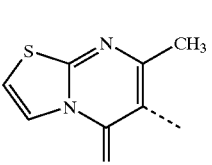 | |
| 6 | B1 | 6-CH$_3$ | O | (CH$_2$)$_2$ | 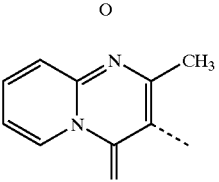 | (E)-2-butenedioate (2:1) |
| 7 | B2 | H | S | (CH$_2$)$_2$ | 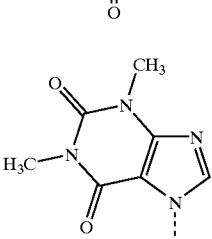 | |
| 8 | B2 | H | S | (CH$_2$)$_3$ | 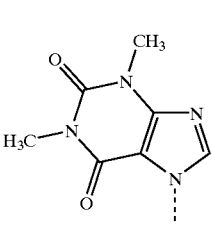 | |

TABLE 1-continued
lists compounds of formula (I) which were prepared according to one of the above examples.
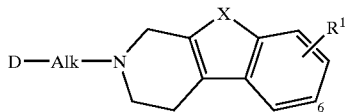
| Co. No. | Ex. No. | R¹ | X₁ | Alk | D | Salt form |
|---|---|---|---|---|---|---|
| 9 | B2 | H | O | (CH₂)₂ | 1,3-dimethylxanthin-7-yl | |
| 10 | B2 | H | O | (CH₂)₃ | 1,3-dimethylxanthin-7-yl | |
| 11 | B2 | H | O | (CH₂)₄ | 1,3-dimethylxanthin-7-yl | |
| 12 | B2 | H | S | (CH₂)₃ | quinazoline-2,4-dion-3-yl | |
| 13 | B2 | H | S | (CH₂)₄ | quinazoline-2,4-dion-3-yl | |
| 14 | B2 | H | O | (CH₂)₂ | quinazoline-2,4-dion-3-yl | |
| 15 | B2 | H | O | (CH₂)₃ | quinazoline-2,4-dion-3-yl | |

TABLE 1-continued
lists compounds of formula (I) which were prepared according to one of the above examples.
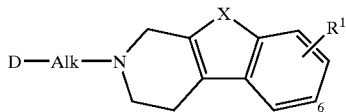
| Co. No. | Ex. No. | R¹ | X₁ | Alk | D | Salt form |
|---|---|---|---|---|---|---|
| 16 | B2 | H | O | (CH₂)₄ | 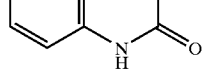 | |
| 17 | B2 | H | S | (CH₂)₃ | 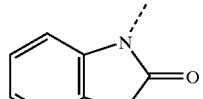 | |
| 18 | B2 | H | O | (CH₂)₃ | 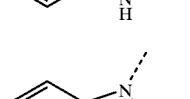 | |
| 19 | B2 | H | O | (CH₂)₄ | 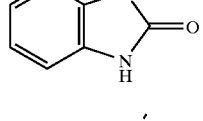 | |
| 20 | B1 | 6-CH₃ | O | (CH₂)₄ | 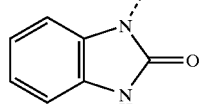 | HCl (1:1) |
| 21 | B1b | 6-Cl | S | (CH₂)₄ | 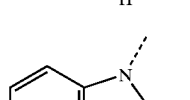 | (E)-2-butenedioate (1:1) |
| 22 | B2 | H | S | (CH₂)₄ | 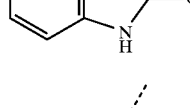 | |
| 23 | B2 | H | S | (CH₂)₂ | 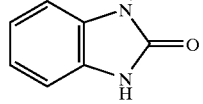 | |
| 24 | B2 | H | O | (CH₂)₂ | 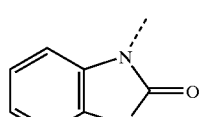 | |

TABLE 1-continued
lists compounds of formula (I) which were prepared according to one of the above examples.
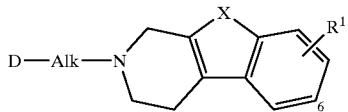
| Co. No. | Ex. No. | R[1] | X[1] | Alk | D | Salt form |
|---|---|---|---|---|---|---|
| 25 | B6 | H | S | (CH$_2$)$_4$ | 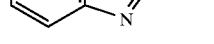 | |
| 26 | B2 | H | S | (CH$_2$)$_5$ |  | |
| 27 | B2 | H | O | (CH$_2$)$_2$ | 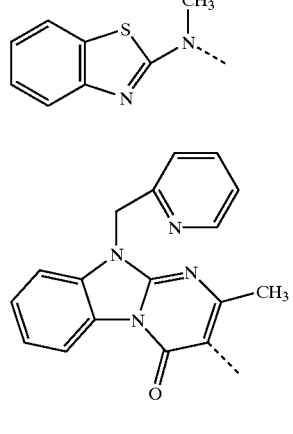 | |
| 28 | B2 | H | O | (CH$_2$)$_2$ | 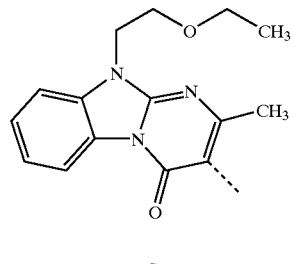 | |
| 29 | B2 | H | O | (CH$_2$)$_2$ | 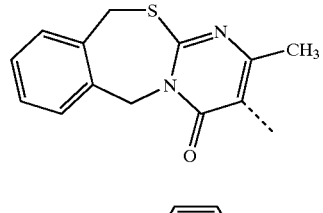 | |
| 30 | B2 | H | S | (CH$_2$)$_2$ | 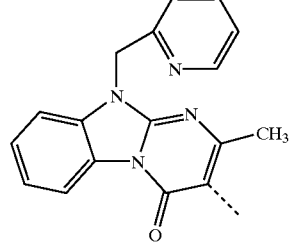 | |

TABLE 1-continued
lists compounds of formula (I) which were prepared according to one of the above examples.
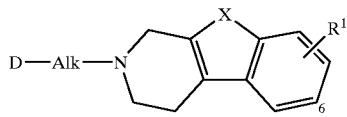
| Co. No. | Ex. No. | R¹ | X₁ | Alk | D | Salt form |
|---|---|---|---|---|---|---|
| 31 | B2 | H | S | (CH₂)₂ | | |
| 32 | B2 | H | S | (CH₂)₂ | | |
| 33 | B8 | H | O | CH₂ | | (E)-2-butenedioate (1:1) |
| 34 | B9 | H | S | CH₂ | | |
| 35 | B9 | 6-CH₃ | O | CH₂ | | (E)-2-butenedioate (1:1) |
| 36 | B7 | H | O | (CH₂)₄ | | HCl (1:1) |
| 37 | B1 | 6-CH₃ | O | (CH₂)₂ | | (E)-2-butenedioate (2:1) |
| 38 | B1 | 6-Cl | S | (CH₂)₂ | | |

TABLE 1-continued lists compounds of formula (I) which were prepared according to one of the above examples.

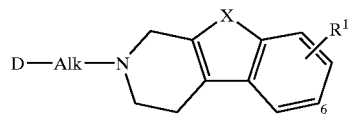

| Co. No. | Ex. No. | R¹ | X₁ | Alk | D | Salt form |
|---|---|---|---|---|---|---|
| 39 | B1 | 6-Cl | S | (CH₂)₂ | 2-methyl-thiazolo[3,2-a]pyrimidin-5(4H)-one-3-yl | |
| 40 | B1 | 6-F | S | (CH₂)₄ | 3-methyl-2-oxo-2,3-dihydro-1H-benzimidazol-1-yl | HCl (1:1) |
| 41 | B3 | 6-F | S | (CH₂)₄ | benzothiazol-2-ylamino | |
| 42 | B1 | 7-OCH₃ | O | (CH₂)₂ | 2-methyl-thiazolo[3,2-a]pyrimidin-5(4H)-one-3-yl | |
| 43 | B1 | 7-OCH₃ | O | (CH₂)₂ | 2-methyl-4-oxo-4H-pyrido[1,2-a]pyrimidin-3-yl | |
| 44 | B2 | 6-CH₃ | O | (CH₂)₄ | benzothiazol-2-ylamino | (E)-2-butenedioate (2:5) |
| 45 | B2 | 6-CH₃ | O | (CH₂)₄ | benzo[d]isothiazol-3-ylamino | HCl (1:2) |
| 46 | B9 | 7-OCH₃ | O | CH₂ | 4-phenoxyphenyl | (E)-2-butenedioate (1:1) |

TABLE 1-continued
lists compounds of formula (I) which were prepared according to one of the above examples.
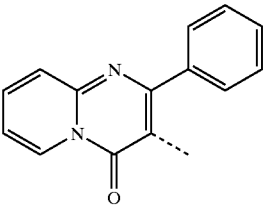
| Co. No. | Ex. No. | R¹ | X₁ | Alk | D | Salt form |
|---|---|---|---|---|---|---|
| 47 | B1 | H | O | (CH₂)₂ | 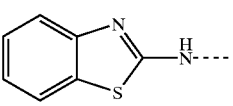 | (E)-2-butenedioate (2:1) |
| 48 | B2 | H | O | (CH₂)₄ | 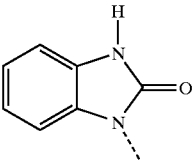 | (E)-2-butenedioate (1:1) |
| 49 | B2 | H | O | (CH₂)₂ | 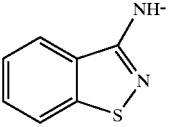 | |
| 50 | B4 | H | O | (CH₂)₄ | 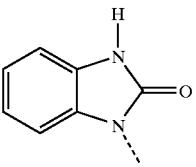 | HCl (1:2) |
| 51 | B1 | 7-OCH₃ | O | (CH₂)₄ | 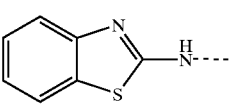 | HCl (1:1), H₂O (1:1) |
| 52 | B2 | 7-OCH₃ | O | (CH₂)₄ | | (E)-2-butenedioate (1:1) |
| 53 | B2 | H | S | (CH₂)₂ | 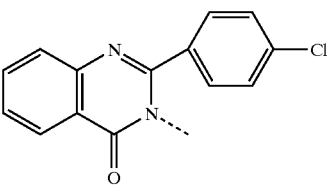 | (E)-2-butenedioate (2:1) |
| 54 | B2 | H | S | (CH₂)₂ | 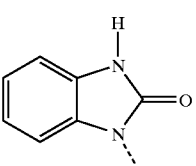 | |

TABLE 1-continued lists compounds of formula (I) which were prepared according to one of the above examples.

| Co. No. | Ex. No. | $R^1$ | $X_1$ | Alk | D | Salt form |
|---|---|---|---|---|---|---|
| 55 | B4 | 7-OCH$_3$ | O | (CH$_2$)$_4$ | benzothiazol-2-ylamino | HCl (1:1); H$_2$O (1:1) |
| 56 | B1 | H | S | (CH$_2$)$_2$ | 2-phenyl-4-oxo-4H-pyrido[1,2-a]pyrimidin-3-yl | |
| 57 | B2 | H | O | (CH$_2$)$_2$ | 2-(4-chlorophenyl)-4-oxo-quinazolin-3-yl | (E)-2-butenedioate (2:1) |
| 58 | B5 | 6-CH$_3$ | O | (CH$_2$)$_4$ | benzo[d]isoxazol-3-ylamino | (E)-2-butenedioate (1:1) |
| 59 | B1 | 7-Cl | O | (CH$_2$)$_2$ | 2-methyl-4-oxo-4H-pyrido[1,2-a]pyrimidin-3-yl | (E)-2-butenedioate (1:1) |
| 60 | B1 | 7-Cl | O | (CH$_2$)$_2$ | 2-methyl-7-oxo-7H-thiazolo[3,2-a]pyrimidin-6-yl | (E)-2-butenedioate (1:1) |
| 61 | B9 | 7-Cl | O | CH$_2$ | 4-phenoxyphenyl | (E)-2-butenedioate (1:1) |
| 62 | B1 | 7-Cl | O | (CH$_2$)$_4$ | 2-oxo-2,3-dihydro-1H-benzimidazol-1-yl | HCl (1:1) |

TABLE 1-continued lists compounds of formula (I) which were prepared according to one of the above examples.

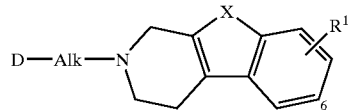

| Co. No. | Ex. No. | R¹ | X₁ | Alk | D | Salt form |
|---|---|---|---|---|---|---|
| 63 | B5 | 7-Cl | O | (CH₂)₄ | benzisoxazol-3-yl-NH— | HCl (1:2) |
| 64 | B3 | 6-Cl | S | (CH₂)₄ | benzothiazol-2-yl-NH— | |
| 65 | B5 | 7-OCH₃ | O | (CH₂)₄ | benzisoxazol-3-yl-NH— | (E)-2-butenediaote (2:1) |

C. Pharmacological Examples

EXAMPLE C.1

In Vitro Binding Affinity for $\alpha_2$ Receptors

The interaction of the compounds of formula (I) with $\alpha_2$ receptors was assessed in vitro radioligand binding experiments.

In general, a low concentration of a radioligand with a high binding affinity for a particular receptor is incubated with a sample of a tissue preparation enriched in a particular receptor or with a preparation of cells expressing cloned human receptors in a bufferred medium. During the incubation, the radioligand binds to the receptor. When equilibrium of binding is reached, the receptor bound radioactivity is separated from the non-bound radioactivity, and the receptor bound activity is counted. The interaction of the test compounds with the receptor is assessed in competition binding experiments. Varius concentrations of the test compound are added to the incubation mixture containing the receptor preparation and the radioligand. Binding of the radioligand will be inhibited by the test compound in proportion to its binding affinity and its concentration.

The radioligand used for $\alpha_{2A}$, $\alpha_{2B}$ and $\alpha_{2C}$ receptor binding is ³H-rauwolscine and the receptor preparation used is the Chinese Hamster Ovary (CHO) cell expressing cloned human $\alpha_{2A}$, $\alpha_{2B}$ and $\alpha_{2C}$ receptors.

From the compounds that were tested, compound No. 1, 5, 7, 8, 11, 12, 13, 16, 17, 19, 24, 28, 29, 20, 32, 33 and 36 produced an inhibition of each of the three receptors of more than 50% at a test concentration ranging between $10^{-6}$ M and $10^{-9}$ M.

D. Composition Examples

"Active ingredient" (A.I.) as used throughout these examples relates to a compound of formula (I), a pharmaceutically acceptable addition salt or a stereochemically isomeric form thereof.

EXAMPLE D.1

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is substequently filled into 1000 suitable hardened gelatin capsules, each comprising 20 mg of the A.I.

EXAMPLE D.2

Film-coated Tablets

Preparation of Tablet Core

A mixture of 100 g of the A.I., 570 g lactose and 200 g starch is mixed well and thereafter humidified with a solution of 5 g sodium dodecyl sulfate and 10 g polyvinyl-pyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinyl-pyrrolidone and 30 ml of concentrated colour suspension and the whole is homogenated. The tablet cores are coated with the thus obtained mixture in a coating apparatus.

EXAMPLE D.3

Oral solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% sodium saccharin were dissolved in 0.5 of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE D.4

Injectable Solution 1.8 Grams methyl 4-hydroxybenzoate and 0.2 grams propyl 4-hydroxybenzoate were dissolved in about 0.5 of boiling water for injection. After cooling to about 50° C. there were added while stirring 4 grams lactic acid, 0.05 grams propylene glycol and 4 grams of the A.I. The solution was cooled to RT and supplemented with water for injection q.s. ad 1 l, giving a solution comprising 4 mg/ml of A.I. The solution was sterilized by filtration and filled in sterile containers.

What is claimed is:

1. A compound having the formula

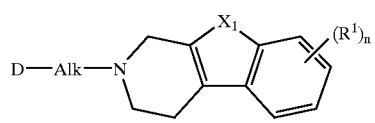
(I)

a N-oxide form, a pharmaceutically acceptable addition salt or a stereochemically isomeric forms thereof, wherein:

Alk is $C_{1-6}$alkanediyl;

n is 1 or 2;

$X_1$ is —O—, —S—, —S(=O)— or —S(=O)$_2$—;

each $R^1$ is independently hydrogen, halogen, $C_{1-6}$alkyl, nitro, hydroxy or $C_{1-4}$alkyloxy;

D is a radical of formula

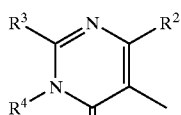
(a)

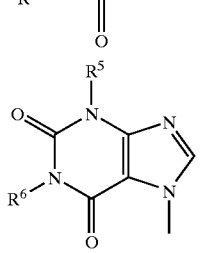
(b)

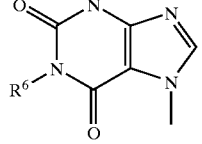
(c)

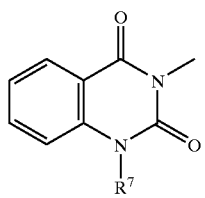
(d)

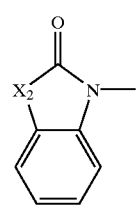

-continued

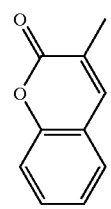
(e)

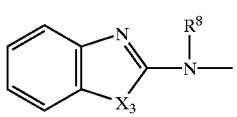
(f)

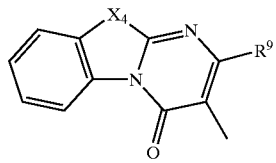
(g)

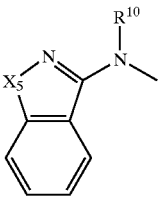
(h)

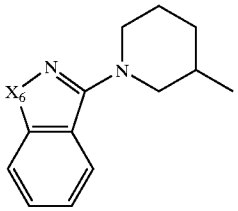
(i)

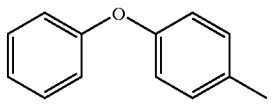
(j)

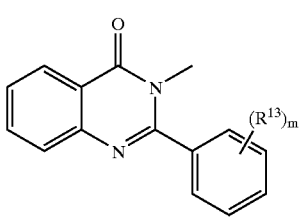
(k)

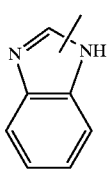
(l)

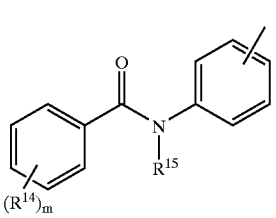
(m)

-continued

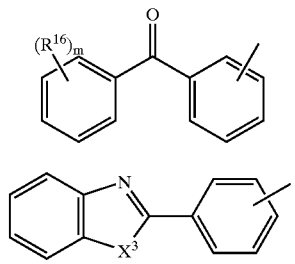

wherein
each m independently is 0, 1 or 2;
$X_2$ is —O— or —$NR^{11}$—;
each $X_3$ independently is —O—, —S— or —$NR^{11}$—;
$X_4$ is —O—, —S—, —$CH_2$—S— or —$NR^{12}$—;
$X_5$ and $X_6$ each independently are —$CH_2$—, —O—, —S— or —$NR^{11}$—;
$R^2$ is hydrogen, $C_{1-6}$alkyl, aryl or aryl$C_{1-6}$alkyl;
$R^3$ is hydrogen, $C_{1-6}$alkyl, $C_{1-6}$alkyloxy, $C_{1-6}$alalkylthio, amino or mono- or di($C_{1-6}$alkyl)amino;
$R^4$, $R^5$, $R^6$, $R^7$, $R^8$, $R^9$, $R^{10}$, $R^{11}$ and $R^{15}$ each independently are hydrogen or $C_{1-6}$alkyl;
$R^{12}$ is hydrogen, $C_{1-6}$alkyl, $C_{1-6}$alkyloxy$C_{1-6}$alkyl or pyridinyl$C_{1-6}$alkyl;
$R^{13}$, $R^{14}$ sand $R^{16}$ each independently are halo or $C_{1-6}$alkyl;
$R^3$ and $R^4$ taken together may form a bivalent radical —$R^3$—$R^4$— formula —$CH_2$—$CH_2$—$CH_2$—  (a-1);
—$CH_2$—$CH_2$—$CH_2$—$CH_2$—  (a-2);
—CH=CH—$CH_2$—  (a-3);
—$CH_2$—CH=CH—  (a-4) or
—CH=CH—CH=CH—  (a-5);

wherein one or two hydrogen atoms of said radicals (a-1) to (a-5) each independently may be replaced by halo, $C_{1-6}$alkyl, aryl$C_{1-6}$alkyl, trifluoromethyl, amino, hydroxy, $C_{1-6}$alkyloxy or $C_{1-10}$alkylcarbonyloxy; or where possible, two geminal hydrogen atoms may be replaced by $C_{1-6}$alalkylidene or aryl$C_{1-6}$alkylidene; or —$R^3$—$R^4$— may also be —S—$CH_2$—$CH_2$—  (a-6);
—S—$CH_2$—$CH_2$—$CH_2$—  (a-7);
—S—CH=CH—  (a-8);
—NH—$CH_2$—$CH_2$—  (a-9);
—NH—$CH_2$—$CH_2$—$CH_2$—  (a-10);
—NH—CH=CH—  (a-11);
—NH—CH=N—  (a-12);
—S—CH=N—  (a-13) or
—CH=CH—O—  (a-14);

wherein one or where possible two or three hydrogen atoms in said radicals (a-6) to (a-14) each independently may be replaced by $C_{1-6}$alkyl or aryl; and aryl is phenyl or phenyl substtituted with one, two or three substtituents selected from halo, hydroxy, nitro, cyano, trifluoromethyl, $C_{1-6}$alkyl, $C_{1-6}$alkyloxy, $C_{1-6}$alalkylthio, mercapto, amino, mono- and di($C_{1-6}$alkyl)amino, carboxyl, $C_{1-6}$alkyloxycarbonyl and $C_{1-6}$alkylcarbonyl.

2. A compound according to claim 1 wherein D is a radical of formula (a), (b ), (c), (d), (e), (f), (g), (h), (i), (j), (k) or (l); m is 0; and aryl is phenyl or phenyl substtituted with halo or $C_{1-6}$alkyl.

3. A compound according to claim 2 wherein n is 1 and $R^1$ is hydrogen, chloro, fluoro, methyl, methoxy or nitro.

4. A compound according to claim 3 wherein X is —O— or —S—.

5. A compound according to claim 4 wherein Alk is methylene, 1,2-ethanediyl, 1,3-propanediyl, 1,4-butanediyl or 1,5-pentanediyl.

6. A compound according to claim 5 wherein D is a radical of formula (a) wherein $R^2$ is aryl or methyl and wherein $R^3$ and $R^4$ are taken together to form a bivalent radical of formula (a-5) or (a-8); or D is a radical of formula (b) wherein $R^5$ and $R^6$ are $C_{1-6}$alkyl; or D is a radical of formula (e); or D is a radical of formula (d) wherein $X_2$ is —$NR^{11}$— and $R^{11}$ is hydrogen; or D is a radical of formula (e); or D is a radical of formula (f) wherein $X_3$ is —S— and $R^8$ is hydrogen or $C_{1-6}$alkyl; or D is a radical of formula (g) wherein $X_4$ is —$CH_2$—S— or $NR^{12}$—and $R^{12}$ is $C_{1-6}$alkyloxy$C_{1-6}$alkyl or pyridinyl$C_{1-6}$alkyl; or D is a radical of formula (h) wherein $X_5$ is —O— or S— and $R^{10}$ is hydrogen; or D is a radical of formula (j); or D is a radical of formula (k) wherein m is 1 and $R^{13}$ is halo.

7. A compound according to claim 1 wherein the compound is

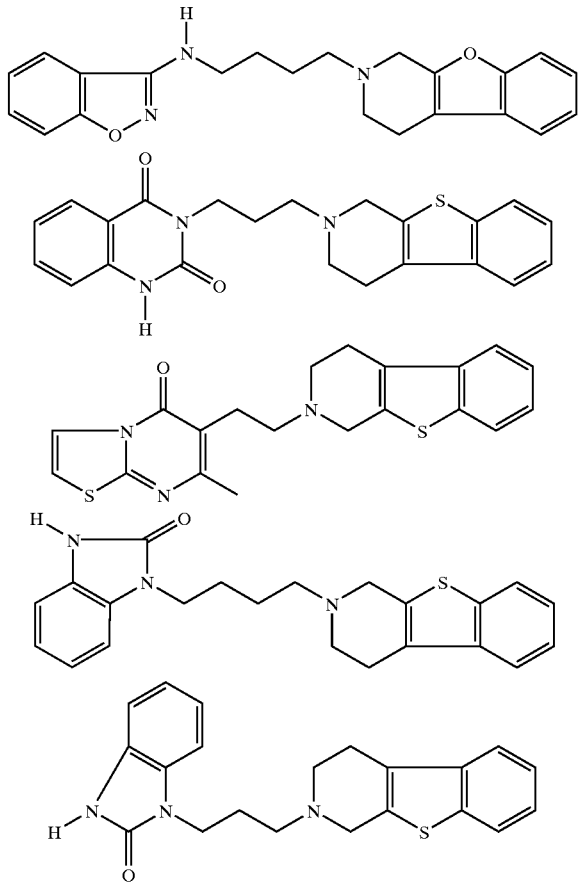

-continued

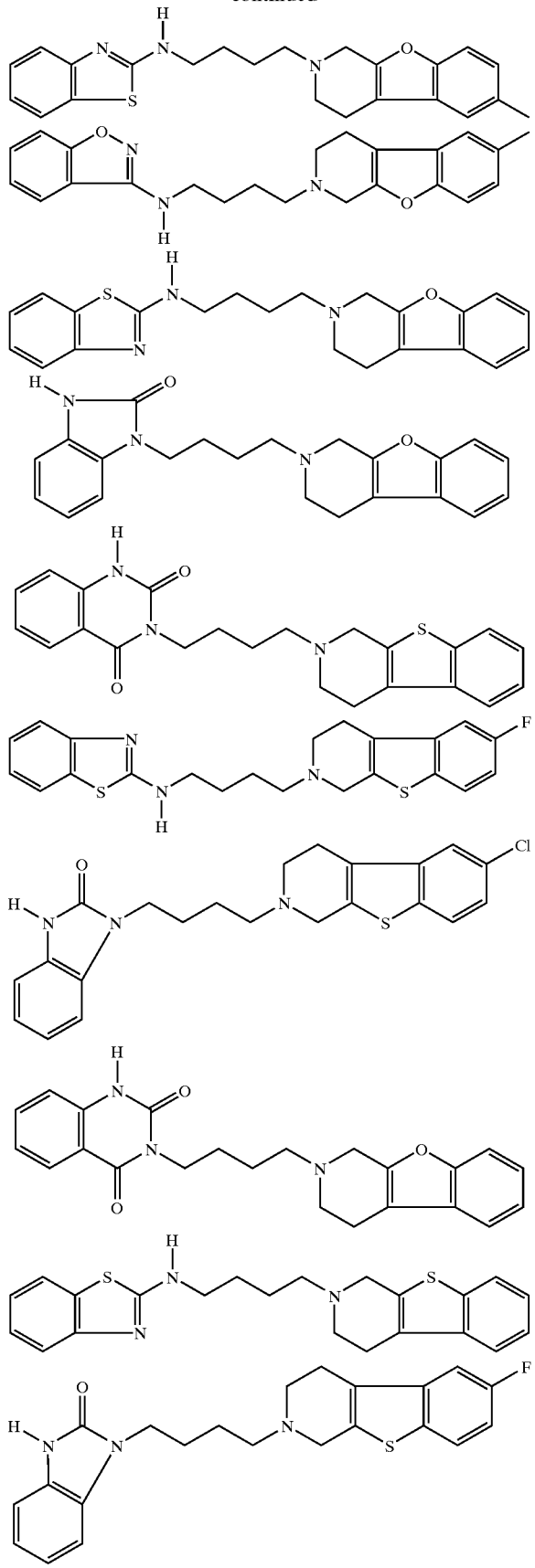

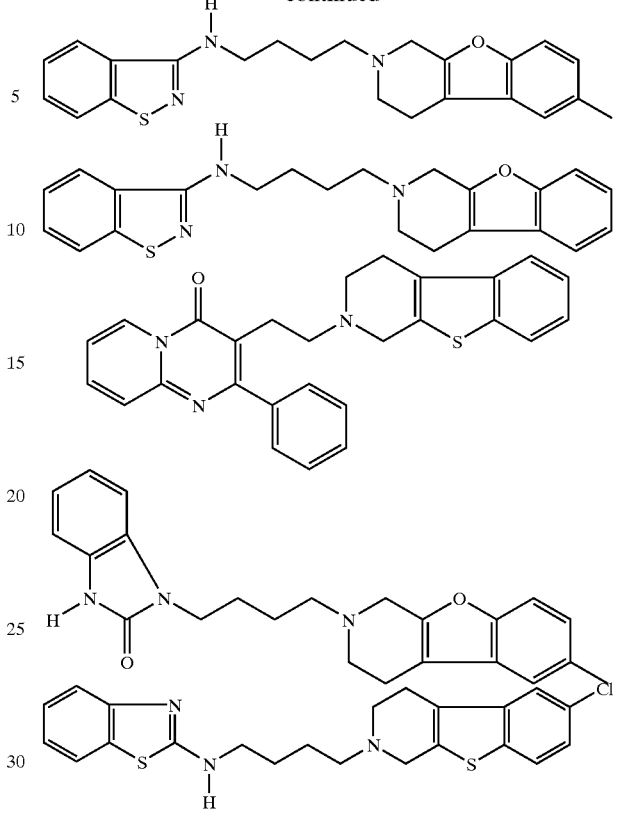

or a N-oxide form, a pharmaceutically acceptable addition salt or a stereochemically isomeric forms thereof.

8. A composition comprising a pharmaceutically acceptable carrier and, as active ingredient, a therapeutically effective amount of a compound as claimed in claim 1.

9. A process for preparing a composition comprising combining a compound of claim 1 as the active ingredient with a pharmaceutically acceptable carrier.

10. A process for preparing a compound according to claim 1, characterized by, a) N-alkylating an intermediate of formula (II) with an alkylating reagent of formula (III)

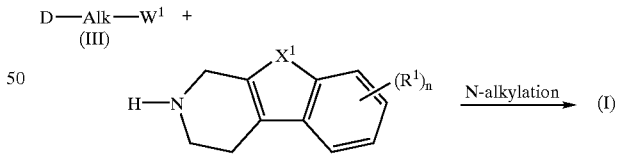

wherein $W^1$ is a suitable leaving group and D, Alk, $X_1$, n and $R^1$ are as defined in claim 1, in a reaction-inert solvent, in the presence of a base and optionally in the presence of a catalyst;

b) N-alkylating an amine of formula (IV) with an intermediate of formula (V)

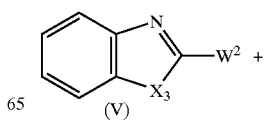

-continued

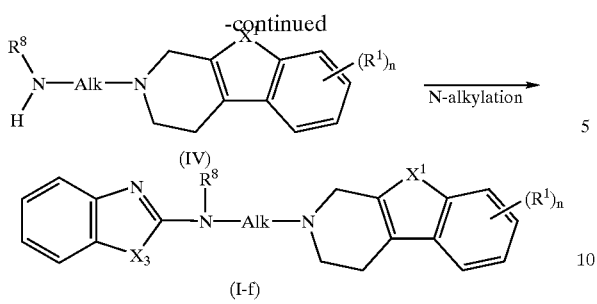

wherein $W^2$ is an appropriate reactive leaving group and D, Alk, $X_1$, $X_3$, n, $R^1$ and $R^8$ are as defined in claim 1; thus forming a compound of formula (I-f).

c) reductive N-alkylating an intermediate of formula (II) with an aldehyde derivative of formula (IV)

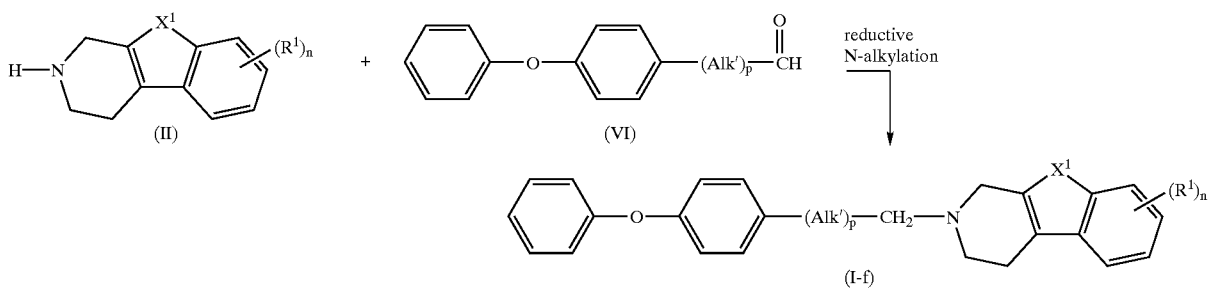

wherein Alk' is $C_{1-5}$alkanediyl, p is 0 or 1 and $X_1$, n and $R^1$ are as defined in claim 1, by reducing a mixture of the reactants in a suitable reaction-inert solvent following art-known reductive N-alkylation procedures, thus forming a compound of formula (I-f);

d) and if desired, converting compounds of formula (I) into each other following art-known transformations, and further, if desired, converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms or N-oxides thereof.

11. A method for treating a disorder selected from the group consisting of depression and Parkinson's disease in a warm-blooded animal in need thereof comprising administering to the warm-blooded animal a therapeutically effective amount of the compound of claim 1.

* * * * *

UNITED STATES PATENT AND TRADEMARK OFFICE
CERTIFICATE OF CORRECTION

PATENT NO. : 6,495,555 B1
DATED : December 17, 2002
INVENTOR(S) : Ludo Edmond Josephine Kennis et al.

It is certified that error appears in the above-identified patent and that said Letters Patent is hereby corrected as shown below:

<u>Column 42,</u>
Line 4, replace "$C_{1-6}$ alalkylthio" with -- $C_{1-6}$ alkylthio --
Line 22, replace "of formula (e);" with -- of formula (c) wherein $R^7$ is hydrogen; --

Signed and Sealed this

Sixth Day of April, 2004

JON W. DUDAS
*Acting Director of the United States Patent and Trademark Office*